United States Patent
Tuschel et al.

(10) Patent No.: US 7,649,618 B2
(45) Date of Patent: Jan. 19, 2010

(54) SYSTEM AND METHOD TO PERFORM RAMAN IMAGING WITHOUT LUMINESCENCE

(75) Inventors: David Tuschel, Monroeville, PA (US); Jingyun Zhang, Upper St. Clair, PA (US)

(73) Assignee: ChemImage Corporation, Pittsburgh, PA (US)

( * ) Notice: Subject to any disclaimer, the term of this patent is extended or adjusted under 35 U.S.C. 154(b) by 312 days.

(21) Appl. No.: 11/728,430

(22) Filed: Mar. 26, 2007

(65) Prior Publication Data

US 2007/0222982 A1 Sep. 27, 2007

Related U.S. Application Data (60) Provisional application No. 60/785,557, filed on Mar. 24, 2006.

(51) Int. Cl.
*G01J 3/44* (2006.01)
*G01N 21/64* (2006.01)
(52) U.S. Cl. .................... 356/73; 356/301
(58) Field of Classification Search .......... 356/73, 356/301
See application file for complete search history.

(56) References Cited

U.S. PATENT DOCUMENTS

| | | | |
|---|---|---|---|
| 5,377,003 A | | 12/1994 | Lewis et al. |
| 5,821,547 A | * | 10/1998 | Talmi et al. ............. 250/458.1 |
| 5,864,397 A | * | 1/1999 | Vo-Dinh ................. 356/301 |
| 7,046,359 B2 | * | 5/2006 | Voigt et al. ............. 356/301 |
| 2002/0149818 A1 | | 10/2002 | Tomofuji et al. |
| 2003/0133105 A1 | | 7/2003 | Gorelik et al. |
| 2005/0221351 A1 | | 10/2005 | Ryu |
| 2006/0028644 A1 | | 2/2006 | Gardner et al. |

(Continued)

FOREIGN PATENT DOCUMENTS

WO 2004106874 12/2004

OTHER PUBLICATIONS

Slater et al, Raman Spectrometry and Its Adaptation to the Industrial Environment, in Handbook of Raman Spectroscopy From the Research Laboratory to the Process Line, edited by Ian R. Lewis and Howell G. M. Edwards, (New York, Marcel Dekker, Inc., 2001), pp. 41-144.*
Optics & Laser Europe, EMCCD cameras take imaging to a new level, Jan. 2006, pp. 29-31.*

\* cited by examiner

*Primary Examiner*—F. L Evans
(74) *Attorney, Agent, or Firm*—Morgan Lewis & Bockius LLP (57) ABSTRACT

A system and method for collecting Raman data sets without the "contaminating" effect of luminescence emitted photons. Using a frame transfer CCD for time resolved data collection, Raman imaging may be performed without photobleaching the sample. The system may include a light source, a frame transfer CCD, an optical lens and at least one controller. The light source illuminates the sample with a plurality of photons to generate scattered photons from the sample. The frame transfer CCD has an image array and a storage array. The optical lens collects scattered photons and directs the scattered photons to the image array. The controller transfers a Raman data set representative of the scattered photons from the image array to the storage array. The frame transfer CCD may be configured so as the image array integrates the scattered photons during a Raman integration time and the controller transfers the Raman data set from the image array to storage array during a parallel transfer time. The sum of the Raman integration time and the parallel transfer time is less than the minimum time it takes to trigger luminescence from the sample.

9 Claims, 9 Drawing Sheets

SYSTEM AND METHOD TO PERFORM RAMAN IMAGING WITHOUT LUMINESCENCE

RELATED APPLICATIONS

This application claims priority to U.S. Provisional Application No. 60/785,557, entitled Raman Imaging Without Luminescence," which was filed on Mar. 24, 2006 and is incorporated herein by reference in its entirety.

FIELD OF DISCLOSURE

The present disclosure relates generally to Raman imaging, and more particularly, to a system to perform Raman imaging without interference from luminescence by using time resolved image capture of Raman scattered and luminescence emitted photons.

BACKGROUND

Chemical imaging is known in the art. One example of an apparatus used for chemical imaging is taught in U.S. Pat. No. 6,002,476, entitled "Chemical Imaging System," to Treado et al. Another example of an apparatus used for chemical imaging is taught in U.S. Pat. No. 7,019,296, entitled "Near Infrared Chemical Imaging Microscope," to Treado et al.

In conventional Raman imaging, a full-frame CCD (Charge Coupled Device) is used. However, with the use of a full-frame CCD, luminescence energy (from the same material and location of the sample) is also captured by the CCD collecting Raman photons, especially when luminescence occurs at the same energy level as the Raman photons. The optical "contaminating" effect of luminescence emissions may be reduced by photobleaching the sample material prior to Raman imaging. However, such additional step of photobleaching may not be always desirable or practicable depending on the sample material at hand. Therefore, it is desirable to devise a Raman imaging system that significantly avoids imaging the interfering luminescence and also avoids requiring sample photobleaching prior to Raman imaging.

SUMMARY

The present disclosure describes a system to perform chemical imaging using a frame transfer CCD. The present disclosure provides for a system for collecting Raman data sets without the "contaminating" effect of luminescence emitted photons. The frame transfer CCD may allow for time resolved data collection and, hence, Raman imaging may be performed without photobleaching a sample. The system may include a light source, a frame transfer CCD, an optical lens and at least one controller. The light source illuminates the sample with a plurality of photons to generate scattered photons from the sample. The frame transfer CCD has an image array and a storage array. In one embodiment, the frame transfer CCD is an electron multiplying CDD. The optical lens collects scattered photons and directs the scattered photons to the image array. The controller transfers a Raman data set representative of the scattered photons from the image array to the storage array.

The frame transfer CCD may be configured so as the image array integrates the scattered photons during a Raman integration time and the controller transfers the Raman data set from the image array to storage array during a parallel transfer time. In one embodiment, the Raman integration time and parallel transfer time overlap. In another embodiment, the Raman integration time fully overlaps with the parallel transfer time. In yet another embodiment, the sample is configured to emit photons in response to illuminating the sample after a luminescence output time period has elapsed since the illumination. In this embodiment, the sum of the Raman integration time and the parallel transfer time is less than the luminescence output time period.

The present disclosure further provides for a system for collecting Raman data sets in the absence of luminescence through time resolved data collection. The system may include a light source, a frame transfer CCD, an optical lens and at least one controller. The laser light source illuminates a sample with a plurality of photons to generate scattered photons and emitted photons from the sample. In one embodiment, the laser light source is a pulsed laser light. The frame transfer CCD has an image array and a storage array. In one embodiment, the frame transfer CCD is an electron multiplying CDD. The optical lens collects scattered photons and emitted photons and directs scattered photons and emitted photons to the image array. The controller transfers a Raman data set representative of the scattered photons from the image array to the storage array and concludes transfer of the Raman data set prior to reception of the emitted photons at the image array via the optical lens. In one embodiment, the system may include a photodiode coupled to the light source and the frame transfer CCD. The photodiode generates gating signals for the light source and the frame transfer CCD to synchronize the illumination of the sample with a collection of the scattered photons at the image array via the optical lens.

The frame transfer CCD may be configured to segregate the collection of Raman data sets and luminescence data sets. This may be accomplished by the image array integrating the scattered photons during a Raman integration time $t_{RI}$. The controller may then transfer the Raman data set from the image array to the storage array during a parallel transfer time $t_{TR}$. The luminescence emitted photons may be generated after a luminescence emission time $t_{LO}$ has elapsed since the illumination by the laser light source. The segregation of Raman and luminescence data sets may occur when $t_{RI} + t_{TR} < t_{LO}$.

In certain embodiments, the systems of the present disclosure may further include a fiber array spectral translator device coupled between the optical lens and the frame transfer CCD detector. The one dimensional end of the fiber array spectral translator device may be coupled to the entrance slit of a spectrograph which disperses scattered photons transferred from the fiber array spectral translator device to facilitate generation of Raman data sets and luminescent date sets by the CCD detector. In certain other embodiments, the systems may include a filter coupled between the optical lens and the frame transfer CCD. The filter sequentially filters the optical lens-collected photons in each of a plurality of predetermined wavelength bands and directs the filtered photons to the frame transfer CCD.

The present disclosure further provides for a method for collecting Raman data sets in the absence of luminescence through time resolved data collection. A sample is illuminated with a plurality of photons to generate Raman scattered photons and emitted photons from the sample. The scattered photons are collected using a CCD detector during a Raman data set collection period without collecting the emitted photons during the Raman data set collection period. In one embodiment, the collection of scattered photons may be performed during or after the illumination of the sample.

In one embodiment, the collecting step may include integrating the received scattered photons during a Raman integration time $t_{RI}$ and transferring the integrated scattered photons during a transfer time $t_{TR}$.

In another embodiment, the method further includes collecting emitted photons after a luminescence emission time $t_{LO}$ has elapsed since illumination of the sample, wherein the Raman data set collection period=$t_{RI}$+$t_{TR}$, and wherein $t_{RI}$+$t_{TR}$<$t_{LO}$.

In accordance with a further aspect, the disclosure provides for another method wherein a sample is illuminated with a plurality of photons to thereby generate Raman scattered photons. A CCD detector collects only those Raman scattered photons that are generated prior to emission of luminescence-related photons from the illuminated sample. The Raman scattered photons are imaged using the CCD detector.

In yet another embodiment, the present disclosure provides for a method wherein a sample containing a luminescent material is illuminated with a plurality of photons to thereby generate Raman scattered photons and luminescence-related photons. The Raman scattered photons are collected using a CCD detector. The collection of the luminescence-related photons by the CCD detector is substantially eliminated during collection of the Raman scattered photons without photobleaching the sample.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DETAILED DESCRIPTION OF THE DISCLOSURE

Reference will now be made in detail to certain embodiments of the present disclosure, examples of which are illustrated in the accompanying figures. It is to be understood that the figures and descriptions of the present disclosure included herein illustrate and describe elements that are of particular relevance to the present disclosure, while eliminating, for the sake of clarity, other elements found in typical chemical imaging systems.

Figure 1:
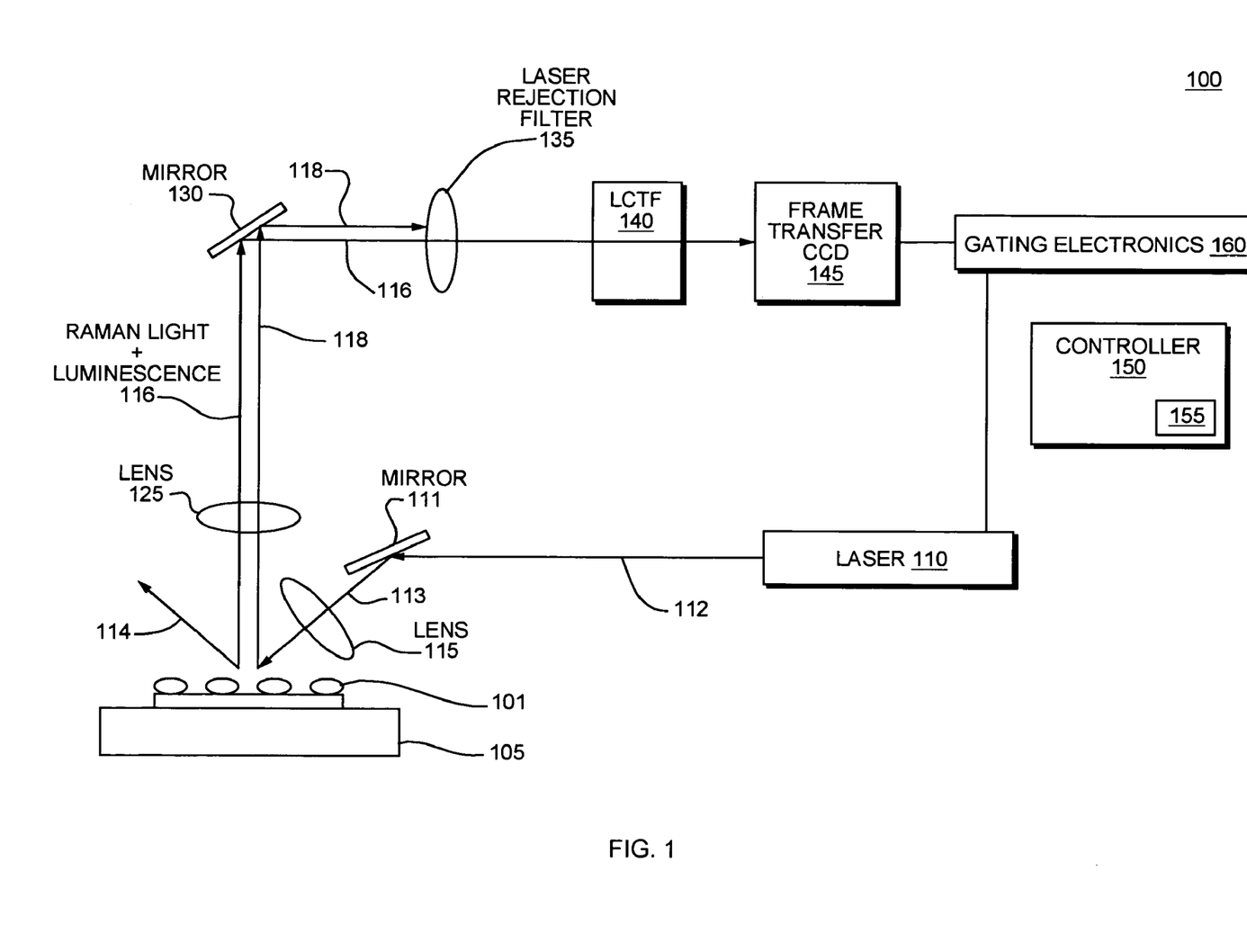
FIG. 1 schematically represents an apparatus according to one embodiment of the disclosure.
Figure 2:
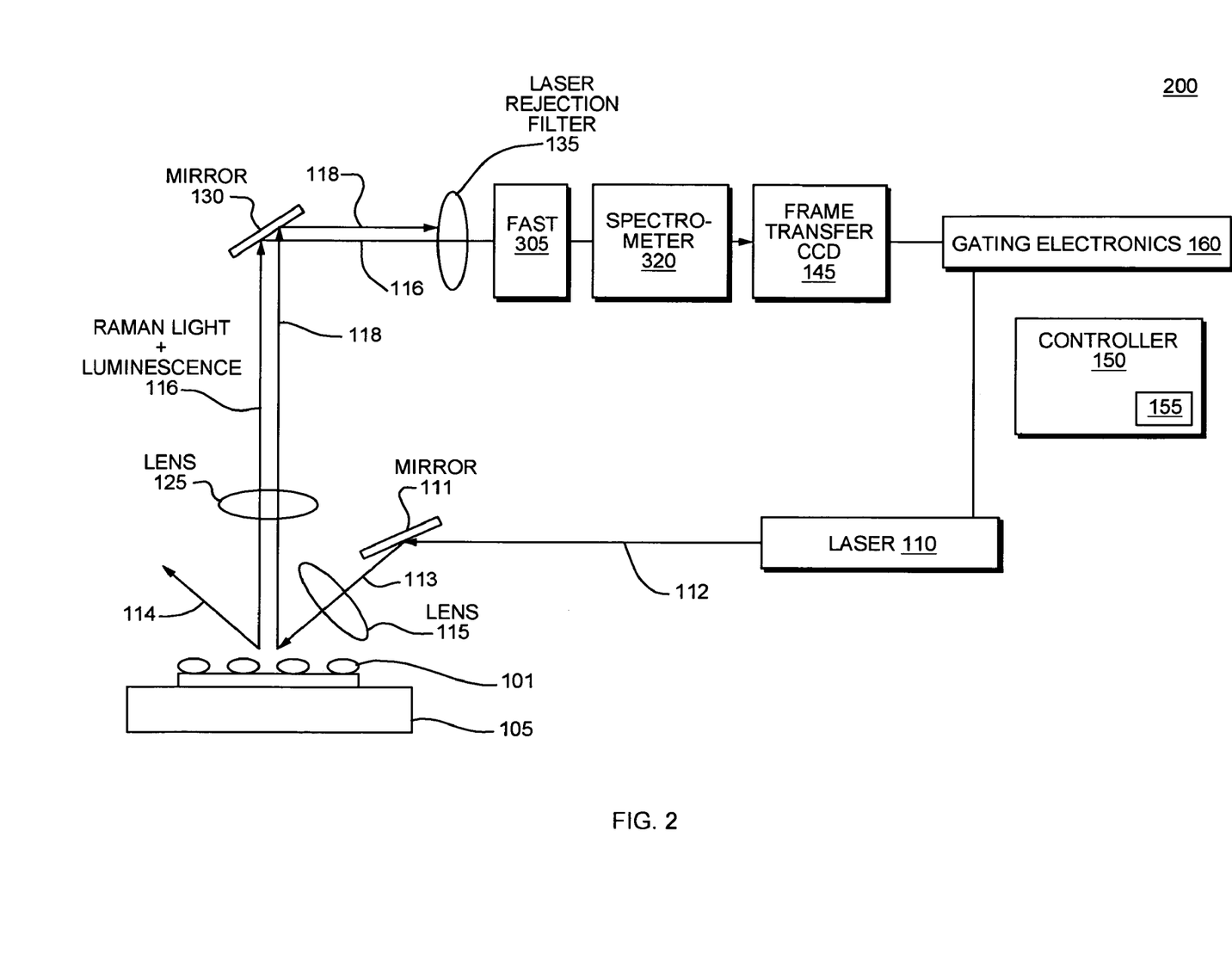
FIG. 2 schematically represents an apparatus according to another embodiment of the disclosure.

FIGS. 1 and 2 schematically represent systems, according to one embodiment of the disclosure, which allow for collecting Raman data sets through time resolved data collection. System 100 may include a laser source 110, a sample 101, a mirror 111, collection lens 125 and a focusing lens 115, mirror 130, filter 140, frame transfer CCD 145, gating electronics 160, controller 150 and machine readable program code 155. System 200 may include a fiber array spectral translator (FAST) device 305 and a spectrometer or spectrograph 320 in place of filter 140. As discussed below, the frame transfer CCD may contain an image array and storage array.

The systems of FIGS. 1 and 2 also include controller 150 and storage medium, such as a hard drive (not shown), containing a machine readable program code 155. The program code 155 functions to allow the controller 150 to configure the components of system 100 and 200, including the illumination source, the optical lens and the frame transfer CCD or EMCCD ("Electron Multiplying CCD") to perform the functions of each component. The controller 150 may configure the light source 110 to illuminate sample 101 with a plurality of photons to generate scattered photons and emitted photons from the sample 101. The optical lens 125 may be configured to collect scattered and emitted photons produced by the sample 101 and to direct the scattered and emitted photons to the image array of the frame transfer CCD 145. The frame transfer CCD 145 may be configured to collect the scattered photons using the image array and to transfer the collected scattered photons to the storage array of the frame transfer CCD. The transfer occurs prior to reception of the emitted photons by the image array via the optical lens 125 as discussed in detail later hereinbelow.

The system 100 of FIG. 1 provides a high optical throughput for imaging low light levels at variable magnification. Referring to FIG. 1, sample 101 is positioned on substrate 105. In one embodiment, the sample 101 includes any sample with a luminescent material. Such a sample may include, for example, a naturally-occurring mineral, a biological sample, a pharmaceutical tablet, etc. Substrate 105 can be any conventional microscopic slide, a hot stage, a microfluidic circuit, or other means for receiving and optionally securing sample 101. The use of a microfluidic circuit in chemical imaging applications is disclosed in U.S. patent application Ser. No. 10/920,320, filed on Aug. 18, 2004, entitled "Method and Apparatus for Chemical Imaging in a Microfluidic Circuit" which is incorporated by reference herein in its entirety. A substantially monochromatic light source 110 is positioned to provide incident light to sample 101. Light source 110 can include any conventional photon source, including a laser (e.g., a UV laser), an LED, and other IR or near IR devices. Light source 110 may also be selected to provide evanescence illumination of the sample. In one embodiment, the line width of the monochromatic light source is in the range of about 15-25 $cm^{-1}$. In another embodiment, the monochromatic light source is a pulsed laser.

Referring still to FIG. 1, it should be noted that the monochromatic light source 110 is positioned to provide incident light along a first optical path 113, which may be at an angle to sample 101 as opposed to light shining orthogonal to sample 101. In other words, the radiation used to illuminate the sample need not pass through the optical train of a conventional microscope or macroscope. Rather, it can illuminate the sample at an oblique angle from above or below sample 101 where photon beam 112 is received and deflected by mirror 111 through lens 115. Lens 115 may optionally be used to focus the light on sample 101. Alternatively, the photon beam 112 may be directed towards the sample 101 without the need for the lens 115.

The multitude of photons in beam 112 reaching sample 101 illuminate the sample and are either scattered or absorbed from different locations on or within the sample 101, which can result in subsequent emission (luminescence) at different wavelengths as well as generation of Raman scattered photons. As known to those skilled in the art, the term "luminescence" includes a wide range of optical processes described using other names. These include: fluorescence, phosphorescence, photoluminescence, electroluminescence, chemiluminescence, sonoluminescence, thermoluminescence and up-conversion. Raman scattered photons and luminescence emitted photons are schematically represented as beam 116 while specularly reflected photons are represented schematically as beam 114. The scattered and emitted photons are produced along a second optical path, defined by photon beam 116, wherein the first optical path 113 may be at an oblique angle with respect to the second optical path.

Optical lens 125 may be positioned along the second optical path 116 to collect photons scattered and/or emitted as represented by photon beam 116. In general, the sample size may determine the choice of light gathering optical lens 125. For example, a microscope lens (not shown) may be employed for analysis of the sub-micron to micrometer specimens. For larger samples, macro lenses can be used. Optical lens 125 (as well as lens 115) may include a simple, reduced resolution/aberration lens with a larger numerical aperture to thereby increase the system's optical throughput and efficiency. Optical lens 125 may be used for gathering and focusing the photons in the received photon beam 116. This may include gathering and focusing both polarized and the non-polarized photons. The collected photons may be directed by optical lens 125 to mirror 130.

In one embodiment, mirror 130 is positioned to direct photon beam 116 to a tunable filter 140. It should be noted that placement of mirror 130 is optional and may be unnecessary in configurations where the tunable filter 140 is positioned above sample 101. With reference to FIG. 1, the tunable filter 140 may include, for example, an electro-optical tunable filter, a liquid crystal tunable filter ("LCTF"), or an acousto-optical tunable filter ("AOTF"). Tunable filter 140 may function to sequentially pass the photons in the beam 116 (e.g., scattered photons, luminescence emitted photons, etc.) into a plurality of predetermined wavelength bands. The plurality of predetermined wavelength bands includes specific wavelengths or ranges of wavelengths. In one embodiment, the predetermined wavelength bands include wavelengths characteristic of the sample undergoing analysis. In another embodiment, the predetermined wavelength bands include wavelengths in the visible light region. In yet another embodiment, the predetermined wavelength bands include wavelengths in the ultraviolet light region. In still another embodiment, the predetermined wavelength bands include wavelengths in the near-infrared light region. The choice of tunable filter depends on the desired optical region and/or the nature of the sample being analyzed. Although an LCTF is illustrated as the tunable filter 140 in FIG. 1, the tunable filter 140 may be selected from other types of tunable filters including, for example, a Fabry Perot angle tuned filter, a Lyot filter, an Evans split element liquid crystal tunable filter, a Solc liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, and a liquid crystal Fabry Perot tunable filter.

Figure 3A:
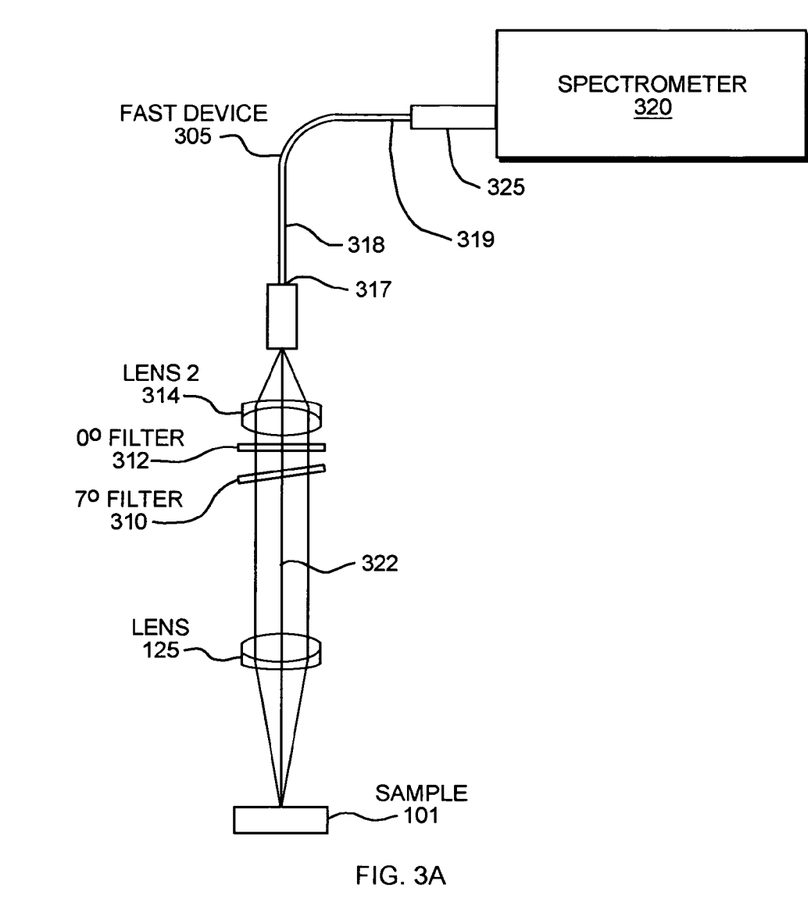
FIG. 3 schematically represents a device used in the systems of the present disclosure.

In another embodiment, mirror 130 may be positioned to direct photon beam 116 to a fiber array spectral translator device ("FAST") 305 as illustrated in FIG. 2. With reference to FIGS. 3A and B, the FAST device may include an optical fiber bundle 318 having a first end 317 and a second end 319. Using the FAST device 305, system 200 may be configured to simultaneously acquire up to thousands of full spectral range, spatially resolved Raman spectra or luminescence spectra. With reference to FIG. 3A, the FAST device 305 is shown relative to objective lens 125. The FAST device 305 may be optically coupled to a first filter 310, a second filter 312, a second lens 314, and a spectrometer or spectrograph 320. The second end 319 of the FAST fiber bundle 318 may be connected to the spectrometer or spectrograph 320. The first lens 125 may act as a collecting lens to collect photons scattered and/or emitted from the sample 101. Lens 125 may collimate the photons produced by the sample projecting the photons into infinity. The first filter 310 may be oriented at an angle of 7° with reference to a plane that is perpendicular to a center optical axis 322, whereas the filter 312 may be oriented at an angle of 0° as illustrated in the embodiment of FIG. 3A. The second lens 314 may be used in combination with the first lens 125 and the filters 310, 312 to form images at the final focal plane of the second lens 314. In the embodiment of FIG. 3A, the first end 317 of the FAST fiber bundle is comprised of a two dimensional non-linear array of optical fibers 316, as illustrated in the exemplary FIG. 3B. The second end 319 of the FAST fiber bundle may be comprised of a curvilinear array of fibers (not shown) wherein the curvilinear may include a straight line or curved line configurations. Thus, in the FAST device 305 in the embodiments of FIGS. 2-3, a two-dimensional array of optical fibers 316 at the first end 317 is converted into a one-dimensional curvilinear fiber stack at the second end 319 so as to effectively convert a two-dimensional field of view (e.g., a field of view of the sample 101) into a curvilinear field of view suitable for further processing by the spectrometer 320.

Figure 3B:
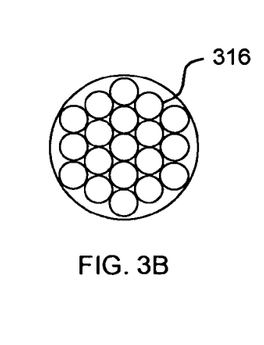

Referring still to FIGS. 3A and 3B, the light collected by the optical assembly including the lenses 125, 314 and filters 310, 312 is focused onto the first end 317 of the fiber bundle. The second end 319 of the fiber bundle may be coupled to spectrometer 320 through a fiber position device 325. In one embodiment, the spectrometer 320 includes a dispersive spectrometer including, for example, a gratings-based dispersive spectrometer. In another embodiment, the fiber array spectral translator device 305 may have 19 collection fibers 316. The entrance slit (not shown) of the spectrometer 320 may be optically coupled to the FAST device 305 to disperse Raman scattered and luminescence emitted photons.

Referring to FIGS. 1 and 2, the laser rejection filter 135 may be positioned prior to tunable filter 140 or FAST device 305 to filter out elastic scattered illumination light represented by beam 118 and to optimize the performance of the system. In other words, rejection filter 135 enables spectral filtering of the photons at the illuminating wavelength. It is noted here that the light beams 116 and 118 are shown separately for ease of illustration only. In practice, all photons (whether laser illumination photons, Raman scattered photons, luminescence emitted photons, etc.) may travel along optical paths that may not be clearly distinguishable from one another or may not be in the form of distinct vertical lines.

With reference to FIGS. 1 and 2, system 100 and system 200 may include a photodiode (not shown) as part of the gating electronics unit 160. The photodiode may be coupled to the light source 110 and the frame transfer CCD 145. The photodiode may function to generate gating signals for the light source 110 and the frame transfer CCD 145 to synchronize the illumination of the sample 101 with the collection of the scattered photons at the frame transfer CCD via the optical lens 125.

Referring still to FIGS. 1 and 2, system 100 and system 200 are shown to include the detector 145. In one embodiment, each detection element (not shown in FIGS. 1-2, but illustrated in the exemplary layouts in FIG. 4) in detector 145 functions to detect photons scattered, and/or emitted from a different spatial location on or within the sample. In one embodiment, the detector 145 produces digital images of the entire view of the sample as processed by tunable filter 140 (in the embodiment of FIG. 1), or by the assembly of the FAST device 305 and the dispersive spectrometer 320 (in the embodiment of FIG. 2).

Detector device 145 may include a frame transfer CCD, an interline transfer CCD or an electron multiplying CCD ("EM-CCD"). In one embodiment, detector 145 generates a Raman data set. The Raman data set may include data representing a plurality of spatially resolved Raman spectra or a plurality of spatially accurate wavelength resolved Raman images from the collected scattered photons. In another embodiment, detector 145 generates a luminescence data set which may include data representing a plurality of spatially resolved luminescence spectra and a plurality of spatially accurate wavelength resolved luminescence images.

Figure 4A:
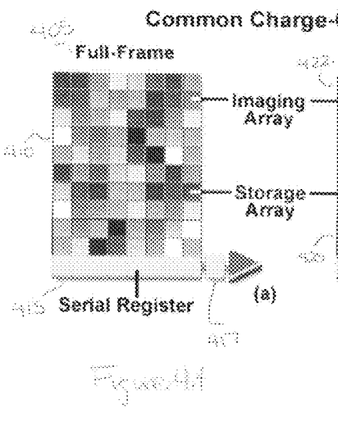
FIGS. 4A-4C schematically represent exemplary CCD architectures.
Figures 4B, 4C:
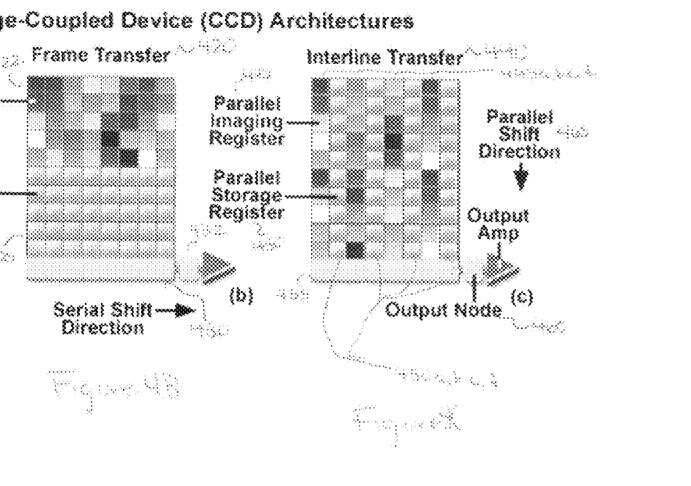

FIGS. 4A, 4B and 4C compare a full frame CCD 405 to a frame transfer CCD 420 and an interline transfer CCD 440. The architectural details shown in FIGS. 4A-4C are significantly simplified to facilitate ease of comparison. The normal functioning of a CCD can be divided into two phases: exposure and readout. FIG. 4A illustrates an exemplary full-frame CCD architecture 405 which may include an image array 410 having a plurality of cells, a serial shift register 415 and an output node 417. During exposure, the full frame CCD 405 passively collects incoming photons, storing electrons in the array of cells 410. After a predetermined exposure time is passed, the cells are read out one line at a time. During the readout phase, contents of cells are shifted down on the entire area of the array 410 to the serial shift register 415. While the contents are shifted, the CCD cells continue to collect light. Thus, in case of the full-frame CCD 405, if the shifting is not fast enough, errors can result from light that fall on a cell whose content was not in its proper position. These errors are referred to as "vertical smear" and cause a strong light source to create a vertical line above and below its exact location. Furthermore, a faster shifting requires a faster readout, and a faster readout can introduce errors in the cell charge measurement, leading to a higher noise level.

A frame transfer CCD (e.g., the CCD 420 in FIG. 4B) may solve both of the above mentioned problems of the full-frame CCD 405: it may substantially eliminate vertical smear, and it also may allow the light collecting CCD portion to continue collecting light while its previous contents are being rapidly read out. A frame transfer CCD has a hidden, not normally used (for light collection), area containing as many cells or detection elements (may also be referred to as "pixels") as the area exposed to light. Frame-transfer CCDs can operate at faster frame rates than full-frame devices because exposure and readout can occur simultaneously with various degrees of overlap in timing.

FIG. 4B illustrates an exemplary architecture of the frame transfer CCD 420. The frame transfer CCD 420 may have architecture similar to the traditional full frame CCD 405, except that the full frame portion of the CCD is now divided into two separate and almost identical areas—the imaging CCD array 422, and the storage CCD array 425—and appropriate timing and control electronics added. The rectangular storage pixel array 425 may be covered by an opaque mask, and may be used as a storage buffer for photoelectrons gathered by the unmasked light-sensitive portion or imaging array 422. It is seen from FIG. 4B that the frame transfer CCD 420 in fact contains two CCDs of the same size—the image array 422, and the storage array 425. Typically, the storage array 425 may be covered by a reflective material such as aluminum. The image array 422 may consist of cells of light-sensitive photodiode register, which acts as the image plane and collects incoming photons projected onto the CCD surface by the camera or microscope lenses (e.g., the lenses 125 and 314 in the embodiment of FIG. 3). The storage array 425 area contains as many cells as the area exposed to light in the imaging array 422. When the exposure time is up, the contents of the cells in the image array CCD 422 are transferred very rapidly to corresponding cells in the storage array CCD 425. In the storage array 425, the transferred charge is safe from any light exposure to image array 422 due to the aluminum or similar opaque coating. The stored charge in storage array 425 of the sensor can be systematically read out at a slower, more efficient rate (to correctly measure the cells' charge) while the next image is simultaneously being exposed to the image array 422. Transfer time from the image array 422 to the shielded storage array 425 may be dependent upon the pixel array sizes, but is typically on the order of 500 microseconds or less.

In FIG. 4B, the storage array 425 is illustrated as a large area of "cells" or "pixels" that have been covered with an opaque metal mask (e.g., an aluminum mask) or light shield (not shown) to prevent any potential interaction with incoming photons (which may be in the process of being collected by the image array portion). A miniature portion of the total image is contained in each pixel element, which may consist of four photodiodes masked with red, green, and blue colored filters as illustrated in more details in the exemplary embodiment of FIG. 5A.

After image data have been collected and converted into electrical potential by the cells in the image array 422, the data are then quickly shifted in a parallel transfer to the corresponding cells in the storage array 425 for readout by a serial shift register 430 to output node 432. Like the full-frame CCD architecture 405, the frame-transfer CCD 420 undergoes readout by shifting image information-containing rows of storage array 425 in a parallel fashion (known as "line transfer"), one row at a time, to the serial shift register 430. The serial register 430 then sequentially shifts each row of image information to an output amplifier as a serial data stream (known as "serial readout"). The entire process—line transfer and serial readout—is repeated until all rows of image data are transferred off the chip, first to a signal output amplifier (not shown in FIG. 4B, but illustrated in FIG. 5A) and then to an analog-to-digital signal converter integrated circuit (not shown). The final image is then reconstructed in a digital format.

It is noted here that the storage array 425 is typically not light sensitive in most frame-transfer CCD designs. However, in some designs, the storage arrays are not equipped with an integral light shield. Rather, a mechanical shutter (not shown) may be provided to make such non-shielded designs opaque to light. A mechanical shutter based frame transfer CCD may be effectively used to quickly capture two sequential images, e.g., to simultaneously acquire images generated at different emission and/or excitation wavelengths.

Referring to FIG. 4C, the exemplary interline-transfer CCD design 440 may contain a parallel imaging register 445 and a parallel storage register 450. The parallel imaging register 445 is formed by image capture columns 445*a, b, c, d*, wherein each column has a plurality of active imaging cells. The parallel storage register 450 is formed by charge-transfer columns 450*a, b, c, d*, wherein each column has a plurality of masked storage-transfer cells. The image capture columns 445*a, b, c, d*, of the parallel imaging register 445 alternate with the charge-transfer columns 450*a b, c, d*, of the parallel storage register 450, over the entire interline-transfer CCD 440. Because each charge-transfer columns 450*a, b, c, d* is located immediately adjacent to each photosensitive cell column 445*a, b, c, d*, the stored charge must only be shifted one column into a transfer channel. This single transfer step can be performed in less than 1 millisecond, after which the charge-transfer columns 450*a, b, c, d* of the storage array may be read out by a series of parallel shifts 465 into a serial register 455 and an output node 460 while the columns 445*a, b, c, d* of the parallel imaging register 445 are being exposed for the next image. The interline-transfer architecture allows very short integration periods through electronic control of exposure intervals, and in place of a mechanical shutter (which may be present in some frame transfer CCDs), the charge-transfer columns 450*a, b, c, d* can be rendered effectively light-insensitive by discarding accumulated charge rather than shifting it to the transfer channels.

Interline-transfer CCDs may include adherent microlenses (not shown), aligned on the CCD surface to cover pairs of image and storage cells, collect light that would normally be lost on the masked cells and focus it on the light-sensitive cells. By combining small pixel size with microlens technology, interline sensors are capable of delivering spatial resolution and light-collection efficiency comparable to full-frame and frame-transfer CCDs. The effective photosensitive area of interline sensors utilizing on-chip microlenses may be increased to 75-90 percent of the surface area. An additional benefit of incorporating microlenses in the CCD structure may be that the spectral sensitivity of the sensor can be extended into the blue and ultraviolet wavelength regions, providing enhanced utility for shorter-wavelength applications, such as fluorescence techniques employing green fluorescent protein (GFP) and dyes excited by ultraviolet light. In order to increase quantum efficiency across the visible spectrum, recent high-performance chips incorporate gate structures composed of materials such as indium tin oxide, which have much higher transparency in the blue-green spectral region. Such non-absorbing gate structures result in quantum efficiency values approaching 80 percent for green light.

Figure 5A:
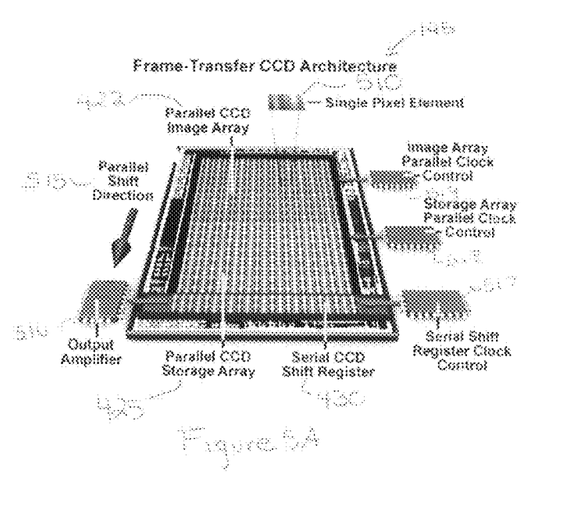
FIGS. 5A-5D schematically represent overall architectural details of two of the CCD devices illustrated in FIG. 4 that may be used in the systems of the present disclosure.

FIG. 5A illustrates an exemplary embodiment of the frame transfer CCD 145 in FIG. 4B in relatively more detail. The image array 422 is located in the upper half of the frame transfer CCD 420. The frame transfer CCD 145 also includes an output amplifier 516, serial shift register clock control 517, storage array parallel clock control 518, image array parallel clock control 519 and serial CCD shift register 430. The storage array 425, located in the lower half of the frame transfer CCD 420, is illustrated as a large area of gray-scale "pixels" that have been covered with an opaque metal mask (e.g., an aluminum mask) or light shield (not shown) to prevent any potential interaction with incoming photons (which may be in the process of being collected by the image array portion). The data from the image array 422 is shifted in a parallel transfer 515 to the corresponding cells in the storage array 425. A miniature portion of the total image is contained in each pixel element 510, which may consist of four photodiodes masked with red, green, and blue colored filters. The image of a single pixel element 510 is presented in the upper right-hand corner of FIG. 5A.

Figure 5B:
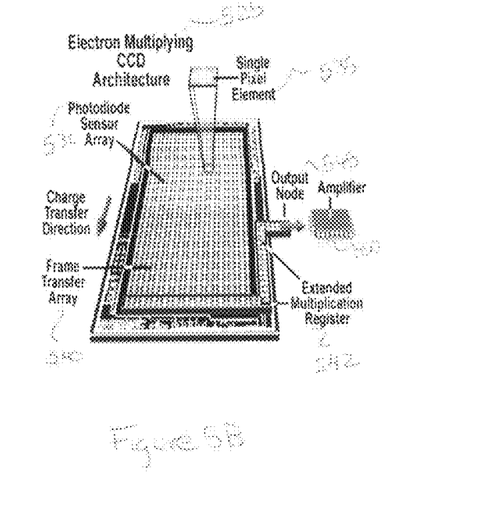
Figure 5C:
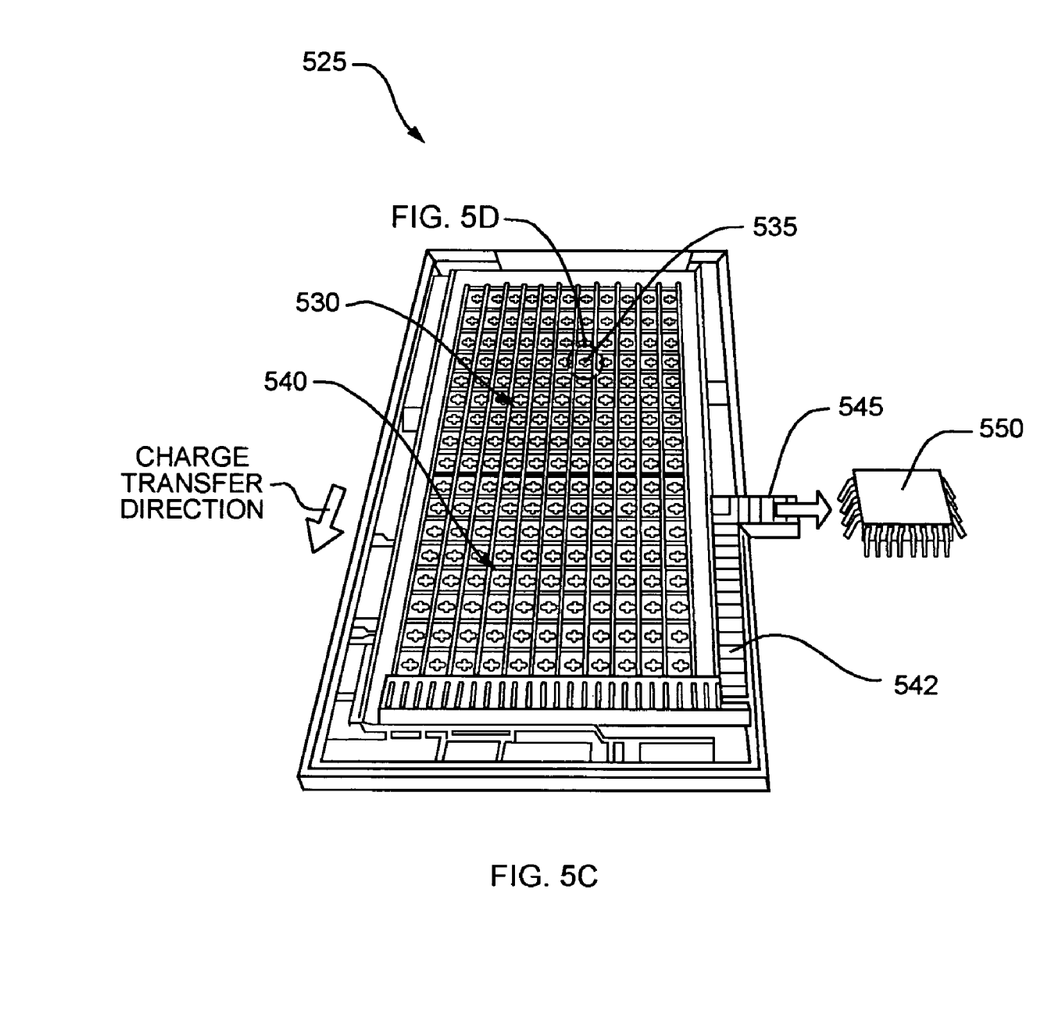
Figure 5D:
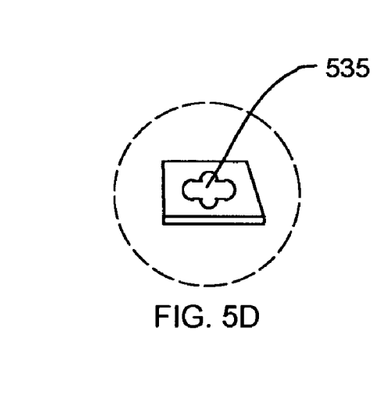
Figure 6A:
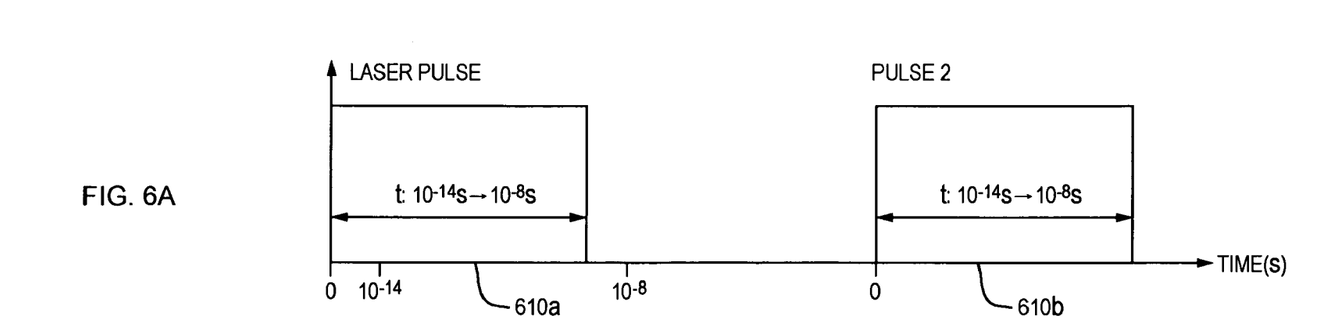
FIG. 6 illustrates exemplary timing waveforms for illumination time, Raman integration time, parallel transfer time and luminescence time.
Figure 6B:
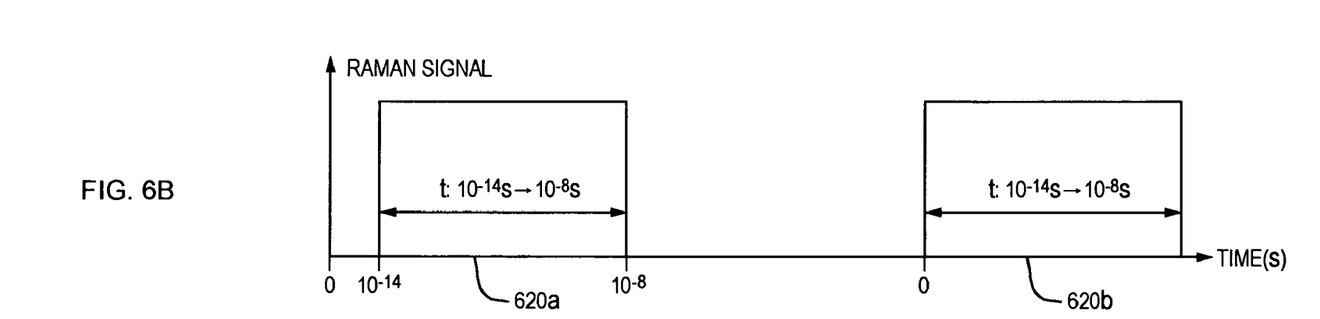
Figure 6C:
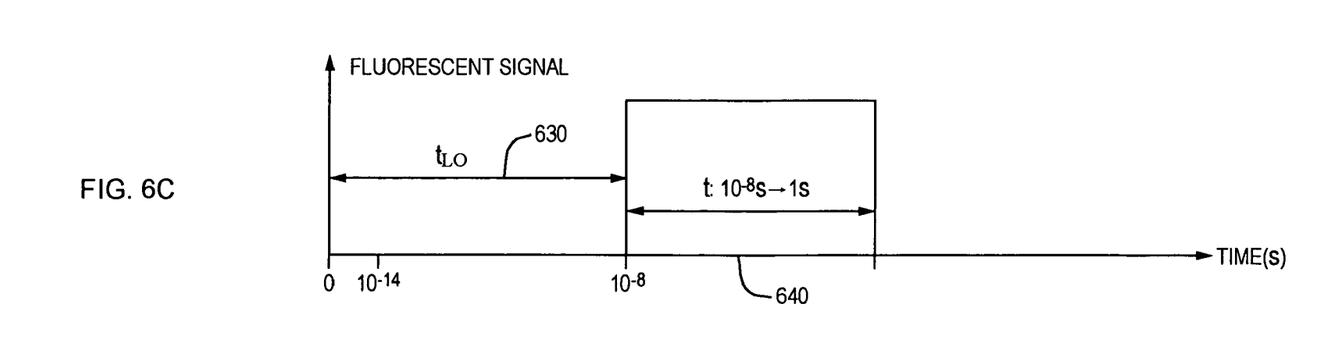
Figure 6D:
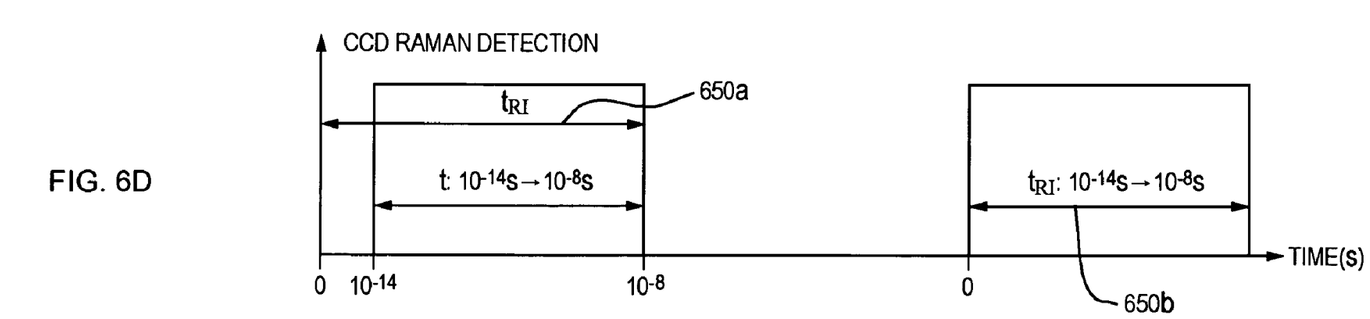
Figure 6E:
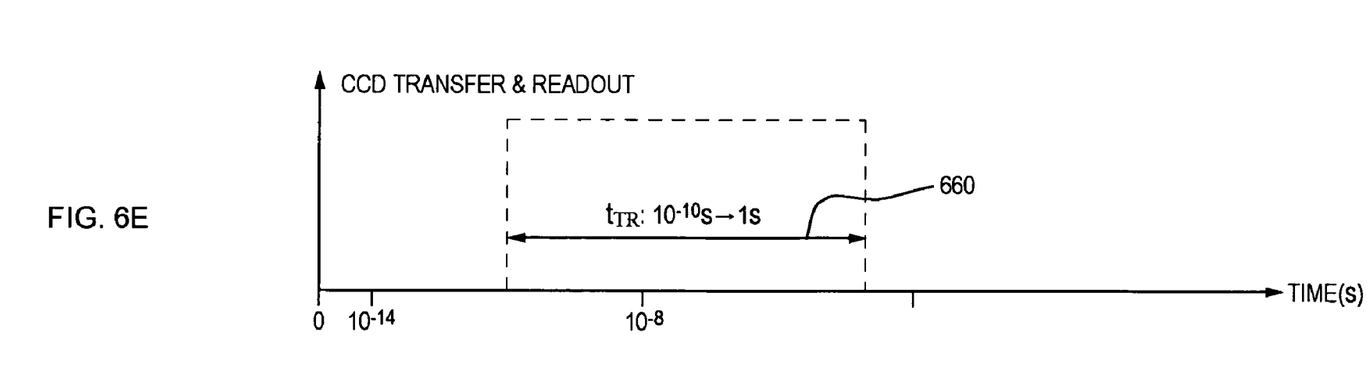

The systems and methods of the present disclosure may also utilize an electron multiplying CCD. The EMCCD 525 may include a photodiode sensor array 530 (image array), frame transfer array 540 (storage array). The photodiode sensor array 530 contains a plurality of pixel elements 535. As shown in FIG. 5B, EMCCD 525 may include a specialized extended serial register (shift register) 542 on the CCD chip that produces multiplication gain through the process of impact ionization in silicon. By elevating photon-generated charge above the read noise of the device, even at high frame rates, the EMCCD 525 has the capability of meeting the needs of ultra-low-light imaging applications without the use of external image intensifiers.

The electron multiplying CCD 525 may incorporate a structural enhancement to amplify the captured light signal before the charge is transferred to the output node 545, which has the effect of reducing the read noise, relative to signal, by the value of the multiplication gain factor. Because very weak specimen light signal levels may produce a charge packet from a single pixel of only a few electrons, even with slow readout from a high-performance CCD, the signal may be lost in read noise. The EMCCD 525, on the other hand, may provide a mechanism to improve signal-to-noise ratio for signal levels below the CCD read-noise threshold.

Electron multiplying CCD sensor 525 may be produced utilizing conventional CCD fabrication techniques by making relatively simple structural modifications. In the EMCCD 525, an electron multiplying structure 542 (in effect, a charge amplifier) may be positioned between the end of the frame transfer array 540 and an output node 545. As noted before, this extended serial register 542 may provide multiplicative gain following detection of photons in the device's active pixel array 535. The EMCCD sensor 525 may also include an amplifier 550.

It is observed here with reference to the exemplary CCD architectures in FIGS. 5A and 5B (and, also, the corresponding architecture in exemplary FIG. 4B) that during the period in which the parallel storage array is being read, the image array may be busy integrating charge for the next image frame. Thus, a frame-transfer device may operate without a shutter or synchronized strobe, allowing for an increase in device speed and faster frame rates. However, frame-transfer CCDs may exhibit some smearing effects which may occur because of the time necessary for transfer of image integration data from the image array to the storage array.

In one embodiment of the present disclosure, a frame-transfer CCD, an interline-transfer CCD, or an EMCCD (instead of a full-frame CCD) is used to accomplish Raman imaging substantially without interfering luminescence based upon time resolved image capture of Raman and luminescence photons originating from the same material and location of the sample. It is known in the art that Raman scattering can occur within femtoseconds ($10^{-15}$ seconds) of illuminating the sample with a laser excitation. However, depending on the luminescent materials present in the sample and the lifetimes of those materials, luminescence-related emissions may not occur until after about $10^{-6}$ to $10^{-3}$ seconds have elapsed since laser excitation of the sample. Thus, there is a temporal difference of about eight orders of magnitude between the timings of Raman scatterings and luminescence emissions. Also, such luminescence-related emissions may last from some milliseconds to even seconds. In other words, there is generally a definite time delay between the onset of Raman scattering and subsequent luminescence emissions. Therefore, in one embodiment of the present disclosure, a high speed frame transfer CCD (e.g., the frame transfer CCD illustrated in the exemplary embodiment of FIG. 5A) is timed with a laser excitation pulse to capture the Raman light and transfer that Raman image frame to the storage array portion of the CCD prior to the occurrence of the luminescence-related emission. Using a high speed frame transfer CCD, the Raman image data can be collected and transferred (to the storage array for subsequent readout) prior to the onset of the time-delayed luminescence.

In one embodiment, the present disclosure relates to photophysical timing differences between Raman scattering and luminescence emission. The present disclosure thus relates to time-resolved Raman spectral imaging using CCD detectors for Raman imaging. The present approach may allow use of any laser excitation wavelength of choosing without interfering luminescence and without the need for photobleaching.

In operation, the image array of the CCD (e.g., the frame transfer CCD 145 in FIGS. 1-2) may be turned on or triggered to collect the data for the extremely-fast occurring Raman event. After the requisite collection/data integration period is over, the collected data may be transferred in parallel to the storage array. In one embodiment, the image array may be turned off, to prevent any further data collection as soon as the transfer is over. In a second embodiment, the image array may be maintained in its "ON" condition to collect luminescence emissions. The luminescence image can be stored after the Raman image data are readout or deleted as desired. The laser (e.g., the laser 110 in FIGS. 1-2) may be pulsed again. This process may be repeated a sufficient number of times to accumulate a Raman image of satisfactory signal-to-noise ratio. In this manner, the Raman portion may be segregated and transferred to the storage array of the CCD without being "contaminated" by luminescence energy.

To accomplish such segregation of Raman and luminescence data, it is desirable that the following timing relationship be satisfied:

$$t_{RI}+t_{TR}<t_{LO} \qquad \text{Eq. 1}$$

where,

"$t_{RI}$" represents the Raman integration time at the image array of the frame transfer CCD (e.g., the CCD 145 in FIGS. 1-2) after the image array (e.g., the image array 422 in FIG. 4B) is triggered to start collecting Raman photons.

"$t_{TR}$" represents the maximum parallel transfer time from the image array to the storage array (e.g., the storage array 425 in FIG. 4B) of the frame transfer CCD (e.g., the CCD 145 in FIGS. 1-2). In one embodiment, $t_{TR}$ may partially overlap with $t_{RI}$, especially when data transfer is initiated substantially simultaneously with image integration. In yet another embodiment, $t_{TR}$ may fully overlap with $t_{RI}$, in which case $t_{RI}+t_{TR}=t_{TR}$. In other embodiment of a partial overlap of $t_{RI}$ and $t_{TR}$, the time value of interest may be the total time in the continuum from triggering of image array to collection of Raman photons to transfer of collected photons to the storage array.

"$t_{LO}$" represents the minimum time it takes for luminescence to trigger (from at least one luminescent material present in the sample 101) after the image array (e.g., the image array 422 in FIG. 4B) is triggered to start accumulating Raman photons. As noted before, the value of $t_{LO}$ may depend on the type and the luminescence lifetime of the material present in the sample.

FIGS. 6(*a*) through 6(*e*) illustrate some exemplary timing waveforms depicting various timing parameters discussed hereinabove. It is noted that the timing values illustrated in FIGS. 6(*a*)-6(*e*) represent a range of values that may be available depending, for example, on the particular frame transfer CCD design, the Raman material at hand, the fluorescence material(s) present in the sample, etc. For example, FIG. 6(*a*) depicts a range of time duration for the laser trigger pulse (e.g., any of the pulses 610*a* and 610*b*) being applied to the frame-transfer CCD (e.g., the CCD 145 in FIGS. 1-2) as well as to the sample at hand. In an alternative embodiment, as mentioned before, a photodiode (not shown) may be used as part of the gating electronics 160 (FIGS. 1-2) to generate gating signals for the laser light source 110 and also for the frame transfer CCD 145 to synchronize the illumination of the sample 101 with a collection of the Raman scattered photons at the image array (e.g., the image array 422 in FIG. 4B) of the frame transfer CCD 145.

In relation to the laser pulses 610*a* and 610*b*, it is seen in FIG. 6(*b*) that the Raman signal scattering 620*a* and 620*b* may occur almost instantaneously (about $10^{-14}$ seconds delay) after the laser excitation is applied to the sample. The Raman scattering may also end almost instantaneously after termination of application of the laser excitation as can be seen from a comparison of FIGS. 6(*a*) and 6(*b*). The duration of detection of this Raman scattering by the image array portion 422 in the CCD 145 may also be of the same duration as shown in FIG. 6(*d*). It is seen in FIG. 6(*e*) that the parallel transfer and data readout process may begin, for example, $10^{-10}$ seconds after the triggering laser pulse (610*a* or 610*b*) and may continue for up to 1 second after the initial time instance at t=0. It is seen from a comparison of FIGS. 6(*d*) and 6(*e*) that the $t_{TR}$ time period 660 may partially overlap with the $t_{RI}$ time period (e.g., 650*a* or 650*b*). FIG. 6(*c*) illustrates exemplary timing values for a fluorescent signal that may get emitted when the laser excitation energy is applied to the sample. As shown in FIG. 6(*c*), the fluorescent signal may get emitted about $10^{-8}$ seconds of delay after application of a laser pulse (e.g., the laser pulse 610*a*) at t=0. This delay may be identified by the parameter $t_{LO}$ 630 as indicated in FIG. 6(*c*). The fluorescence may continue for about 1 second as indicated by the reference numeral 640 in FIG. 6(*c*). In one embodiment, the laser excitation pulse 610*a* or 610*b*, may be applied for a time period slightly less than $t_{LO}$ 630.

It is seen from a comparison of FIGS. 6(*c*)-6(*e*) that the relationship in equation (1) may be satisfied if the values of $t_{RI}$ 650*a* and $t_{TR}$ 660 are properly adjusted in view of the frame-transfer CCD hardware at hand and also in view of the types of fluorescent materials in the sample. In one embodiment, the user may be given control to adjust these values to completely or partially eliminate luminescence-related signal collections at the frame-transfer CCD's image array. It is again emphasized here that the waveforms in FIGS. 6(*a*)-6(*e*) depict various ranges of timing values in ideal conditions. In practice, these values may not be the same as those shown in FIG. 6 and may dictate proper adjustments to the CCD hardware so as to accomplish substantial elimination of luminescence reception at the image array.

It is noted here that a complete elimination of collection of all luminescence-related emissions by the image array (e.g., the image array 422 in FIG. 4B) may not be possible in some embodiments because of potential overlaps in Raman and luminescence collection timings based on the type and nature of the luminescent material(s) in the sample at hand. For example, in case of certain luminescent materials that exhibit luminescence significantly faster than other materials that have a substantially-delayed onset of luminescence, the faster-luminescing material may provide emissions prior to the conclusion of $t_{TR}$ or even during $t_{RI}$. In any event, the more closely the timing relationship in Eq. 1 is observed, the better should be the rejection of luminescence from Raman imaging.

Figure 7:
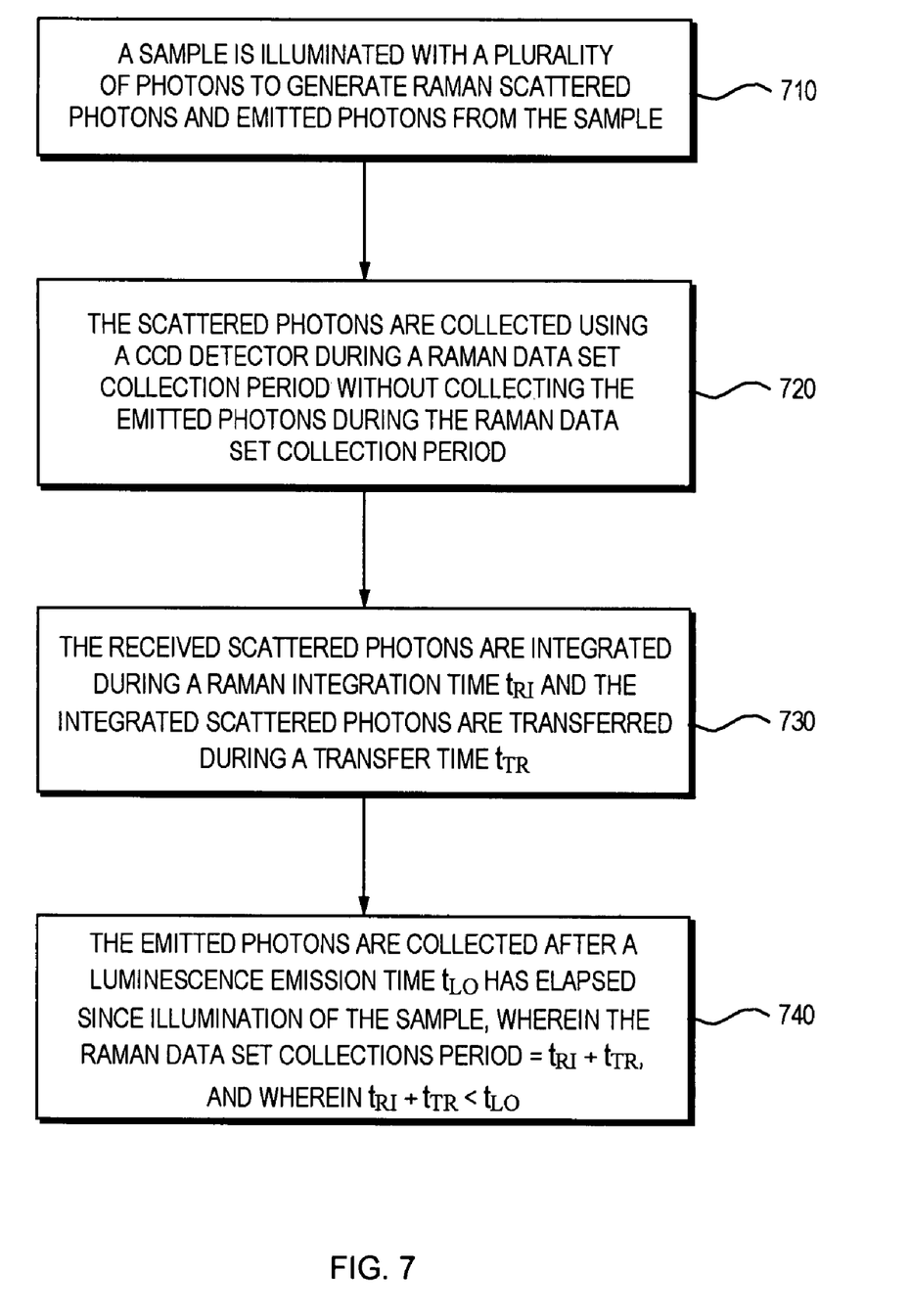
FIG. 7 is a flow chart illustrating an exemplary method of the present disclosure.

FIG. 7 illustrates a flow chart for a method of the present disclosure. In step 710, a sample (e.g., the sample 101 in FIGS. 1-2) is illuminated with a plurality of photons (e.g., from the laser 110 in FIGS. 1-2) to generate Raman scattered photons and emitted photons from the sample. In step 720, the scattered photons are collected using a CCD detector (e.g., the frame-transfer CCD 145 in FIGS. 1-2) during a Raman data set collection period without collecting the emitted photons during the Raman data set collection period. In one embodiment, the collection may be performed during or after the illumination. In step 730, the received scattered photons are integrated during a Raman integration time $t_{RI}$ and the integrated scattered photons are transferred during a transfer time $t_{TR}$. In step 740, the emitted photons are collected after a luminescence emission time $t_{LO}$ has elapsed since illumination of the sample, wherein the Raman data set collection period=$t_{RI}$+$t_{TR}$, and wherein $t_{RI}$+$t_{TR}$<$t_{LO}$.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed:

1. A system comprising:
  a light source that illuminates a sample with a plurality of photons to thereby generate scattered photons from the sample;
  a frame transfer CCD having an image array and a storage array;
  an optical lens that collects said scattered photons and directs said scattered photons to the image array;
  at least one controller that transfers a Raman data set representative of said scattered photons from the image array to the storage array; and
  a fiber array spectral translator device coupled between said optical lens and said frame transfer CCD, wherein said fiber array spectral translator device includes a two-dimensional array of optical fibers drawn into a one-dimensional fiber stack so as to effectively convert a two-dimensional field of view into a curvilinear field of view, and wherein said two-dimensional array of optical fibers is configured to receive said photons collected by said optical lens and transfer the received photons out of said fiber array spectral translator device and to said frame transfer CCD through said one-dimensional fiber stack.

2. The system of claim 1, further comprising: a spectrograph coupled to said one-dimensional fiber stack of said fiber array spectral translator device, wherein an entrance slit of the spectrograph is coupled to said one dimensional fiber stack to disperse said photons transferred out of said fiber array spectral translator device.

3. A system comprising:
  a laser light source that illuminates a sample with a plurality of photons to thereby generate scattered photons and emitted photons from the sample;
  a frame transfer CCD having an image array and a storage array;
  an optical lens that collects said scattered photons and said emitted photons and directs said scattered photons and said emitted photons to the image array;
  at least one controller that transfers a Raman data set representative of said scattered photons from the image array to the storage array and concludes transfer of said Raman data set prior to reception of said emitted photons at said image array via said optical lens; and
  a fiber array spectral translator device coupled between said optical lens and said frame transfer CCD, wherein said fiber array spectral translator device includes a two-dimensional array of optical fibers drawn into a one-dimensional fiber stack so as to effectively convert a two-dimensional field of view into a curvilinear field of view, and wherein said two-dimensional array of optical fibers is configured to receive said scattered and said emitted photons collected by said optical lens and transfer the received photons out of said fiber array spectral translator device and to said frame transfer CCD through said one-dimensional fiber stack.

4. The system of claim 3, further comprising: a spectrograph coupled to said one-dimensional fiber stack of said fiber array spectral translator device, wherein an entrance slit of the spectrograph is coupled to said one dimensional fiber stack to disperse said photons transferred out of said fiber array spectral translator device.

5. A system comprising:
  a laser light source that illuminates a sample with a plurality of photons to thereby generate scattered photons and emitted photons from the sample;
  a frame transfer CCD having an image array and a storage array;
  an optical lens that collects said scattered photons and said emitted photons and directs said scattered photons and said emitted photons to the image array;
  at least one controller that transfers a Raman data set representative of said scattered photons from the image array to the storage array and concludes transfer of said Raman data set prior to reception of said emitted photons at said image array via said optical lens; and
  wherein said frame transfer CCD generates at least one of the following from said collected scattered photons directed from said optical lens: a plurality of spatially resolved Raman spectra and a plurality of spatially accurate wavelength resolved Raman images; and wherein said frame transfer CCD generates at least one of the following from said collected emitted photons received from said optical lens: a plurality of spatially resolved luminescence spectra and a plurality of spatially accurate wavelength resolved luminescence images.

6. A method comprising:
  illuminating a sample with a plurality of photons to thereby generate Raman scattered photons and emitted photons from the sample; and collecting said scattered photons using a CCD detector during a Raman data set collection period without collecting said emitted photons during said Raman data set collection period, wherein said collecting further comprising: configuring a fiber array spectral translator device to receive said Raman scattered photons at a two-dimensional end thereof and transfer said received photons to said CCD detector through a one-dimensional end thereof so as to generate a Raman data set.

7. The method of claim 6, further comprising: dispersing said photons transferred out of said one-dimensional end of said fiber array spectral translator device thereby facilitating generation of at least one of the following: a plurality of spatially resolved Raman spectra or a plurality of spatially accurate wavelength resolved Raman images.

8. A method of comprising:
  illuminating a sample with a plurality of photons to thereby generate Raman scattered photons and emitted photons from the sample; and collecting said scattered photons using a CCD detector during a Raman data set collection period without collecting said emitted photons during said Raman data set collection period, wherein said collecting further comprising: sequentially filtering said Raman scattered photons in each of a plurality of predetermined wavelength bands; and directing the filtered photons for collection thereof by said CCD detector so as to generate a Raman data set.

9. A method comprising:

illuminating a sample with a plurality of photons to thereby generate Raman scattered photons and emitted photons from the sample;

collecting said scattered photons using a CCD detector during a Raman data set collection period without collecting said emitted photons during said Raman data set collection period; and further collecting said emitted photons using said CCD detector after said Raman data set collection period is over; and generating at least one of the following from said collected emitted photons: a plurality of spatially resolved luminescence spectra; and a plurality of spatially accurate wavelength resolved luminescence images.

* * * * *